United States Patent [19]
Amagase

[11] Patent Number: 6,129,918
[45] Date of Patent: *Oct. 10, 2000

[54] METHOD AND PHARMACEUTICAL COMPOSITION FOR REDUCING SERUM HOMOCYSTEINE CONCENTRATION

[75] Inventor: Harunobu Amagase, Mission Viejo, Calif.

[73] Assignee: Wakunaga of America Co., Ltd., Mission Viejo, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 09/133,267

[22] Filed: Aug. 13, 1998

[51] Int. Cl.$^7$ .................................................. A61K 35/78
[52] U.S. Cl. ..................... 424/195.1; 514/824; 514/52; 514/249; 514/345
[58] Field of Search ................. 424/195.1; 514/824, 514/52, 249, 345

[56] References Cited

U.S. PATENT DOCUMENTS

| | | | |
|---|---|---|---|
| 4,737,364 | 4/1988 | Kalogris | 424/195.1 |
| 5,231,114 | 7/1993 | Awazu | 514/707 |
| 5,612,077 | 3/1997 | Hibi | 426/533 |

FOREIGN PATENT DOCUMENTS

| | | | |
|---|---|---|---|
| WO 95/15750 | 6/1995 | WIPO | A61K 31/14 |

OTHER PUBLICATIONS

Agarwal, Med. Res. Reviews 16(1):111–124, 1996.
Boushey, C.J., A Quantitative Assessm't of Plasma Homocysteine as a Risk Factor for Vasc. Disease, JAMA, 1995, 274: 1049–1057.
Perry, I.J., Prosp. study of serum tot. homocysteine conc. and risk of stroke in mid–age British men, The Lancet, 1995, 346: 1395–98.
Malinow, M.R., Homocyst(e)ine and arterial occlusive diseases, Journal of Int. Med., 1994; 236: 603–617.
Verhoef, P., Homocysteine Metabolism and risk of M.I.: Rel. with Vit.'s B6, B12, and Folate, Am. J. of Epidemiology, 1996, 143: 845–859.
McCulley, K.S., Homocysteine, Folate, Vitamin B6, and Cardio. Disease, JAMA, 1998, 279: 392–3.
Arnesen, E., Serum Total Homocysteine and Coronary Heart Disease, INt. Journal of Epidemiology, 1995, 24: 704–9.
Rosenberg, I.H., Homocysteine, Vitamins and Arterial Occ. Disease: An Overview, Am. Inst. of Nutrition. J. Nutr., 1996, 126: 1235S–1237S.
Bratterstrom, L., et al., Homocysteine and cysteine: det.'s of plasma levels in mid–aged and elderly sub.'s, J or Int. Med., 1994 236: 633–641.
Graham, I.M., et al., Plasma Homocysteine as Risk Factor for Vasc. Disease, JAMA, 1997, 277: 1775–1781.
Clarke, R., et al., Hyperhomocysteinemia: An Ind. risk factor for Vasc. Disease, The N.E. J. of Med., 1991, 324: 1149–1155.
Selhub, J., et al., Assoc. between Plasma Homocysteine Conc.'s and Extracranial carotid–artery stenosis, The N.E. J. of Med., 1995 332: 286–91.
Stampfer, M.J. et al., A Prospective Study of Plasma Homocyst(e)ine and Risk of M.I. in US Physicians, JAMA, 1992, 268: 877–881.
Cowley, G., The Heart Attackers, Newsweek, Aug. 11, 1997, 55–60.

*Primary Examiner*—Francisco Prats
*Attorney, Agent, or Firm*—Oblon, Spivak, McClelland, Maier & Neustadt, P.C.

[57] ABSTRACT

A method and composition are described for reducing the elevated plasma homocysteine level in mammals (humans) by oral administration of a therapeutically effective amount of Allium plants or extracts thereof, preferably garlic, with or without one or more vitamins such as $B_6$, $B_{12}$ and folic acid in an acceptable pharmaceutical carrier. Enhanced effectiveness is achieved with a combination of Allium plants or extracts thereof, preferably garlic, with vitamins such as $B_6$, $B_{12}$ and folic acid. The described method and composition are effective for prevention, treating or ameliorating cardiovascular diseases such as myocardial infarction, stroke and multiple arteriosclerosis by the reduction or prevention of high levels of plasma homocysteine, one of the major causes for such diseases. Methods and compositions are disclosed.

9 Claims, No Drawings

METHOD AND PHARMACEUTICAL COMPOSITION FOR REDUCING SERUM HOMOCYSTEINE CONCENTRATION

FIELD OF THE INVENTION

This invention relates to pharmaceutical methods and compositions and more particularly to improved methods and compositions for reducing elevated serum homocysteine concentrations in mammals.

BACKGROUND OF THE INVENTION

Homocysteine, a three carbon sulfidhydral amino acid, (Cys C), CAS Registry Number 52-90-4, having the molecular formula $C_3H_7NO_2S$ [HS—CH2—CH(NH2)—COOH] and a molecular weight of 121.15, has attracted interest because of its relationship to the development of cardiovascular disease. Numerous studies have shown that patients with myocardial infarction, stroke, or peripheral occlusive arterial disease are frequently hyperhomocysteinamic.

This literature includes:

Clarke, R., et al. Hyperhomocysteinemia: An Independent Risk Factor for Vascular Disease. The New England Journal of Medicine, 1991, 324:1149–1155.

Stamfer, M. J., et al. A Positive Study of Plasma Homocyst(e)ine and Risk of Myocardial Infarction in U.S. Patents. JAMA, 1992, 268:877–881.

Malinow, M. R. Homocyst(e)ine and arterial occlusive diseases. Journal of Internal Medicine, 1994, 236:603–617.

Brattstrom, L., et al. Homocysteine and cysteine: determinants of plasma levels in middle-aged and elderly subjects. Journal of Internal Medicine, 1994, 236:633–641.

Arnesen, E., et al. Serum Total Homocysteine and Coronary Heat Disease. International Journal of Epidemiology, 1995, 24:704–709.

Selhub, J., et al. Association Between Plasma Homocysteine Concentrations And Extracranial Carotid-Artery Stenosis. The New England Journal of Medicine, 1995, 332:286–291.

Perry, I. J., et al. Prospective study of serum total homocysteine concentration and risk of stroke in middle-aged British men. Lancet, 1995, 346:1395–1398.

Boushey, C. J., et al. A Quantitative Assessment of Plasma Homocysteine as a Risk Factor for Vascular Disease. JAMA, 1995, 274:1049–1057.

McCulley, K. S. Homocysteine, Foliate, Vitamin $B_6$, and Cardiovascular Disease. JAMA, 1996, 279:392–393.

Verhoef, P., et al. Homocysteine Metabolism and Risk of Myocardial Infarction: Risk with Vitamins $B_6$, $B_{12}$ and Foliate. American Journal of Epidemiology, 1996, 143:845–859.

Cowley, G. The Heart Attackers. Newsweek, Aug. 11, 1997, 54–60.

Rosenberg, I. H., et al. Colloquium: Homocyst(e)ine, Vitamins and Arterial Occlusive Diseases. American Institute of Nutrition. J. Nutr., 1996, 126:1235S–1300S.

Graham, I. M., et al. Plasma Homocysteine as a Risk Factor for Vascular Disease. JAMA, 1997, 277:1775–1791.

It has been reported that an elevated plasma concentration of homocysteine increases the risk for coronary, peripheral and cerebral vascular diseases. It is now known that mild hyperhomocysteinemia is a risk factor independent of cholesterol, smoking status, and systolic blood pressure for cardiovascular disease, thrombotic events and atherosclerosis.

Quite recently, both of two prospective studies, the U.S. Physicians' Study and the Tromoso Study, showed hyperhomocysteinemia to be an independent risk factor for myocardial infarction. Ueland et al. showed that fasting plasma concentration of homocysteine in vascular disease patients was 31% higher than normal subjects. Similarly, in the Physicians' Health Study, Stampfer et al observed that men with myocardial infarction had a higher plasma homocysteine concentration than those free of infarction. More strikingly, they found that even a small increase in plasma homocysteine concentration (i.e., 1.7 mol/L or 12% above the upper limit of normal range) increased the risk for acute myocardial infarction by more than three-fold. The most recent epidemiological study by Selhub et al. demonstrated that the odd ratio for carotid-artery stenosis of greater than 25% was 2.0 for subjects with homocysteine of 14.4 mol/L as compared to those with 9.1 mol/L. Interestingly, the study revealed that the prevalence of stenosis is inversely related to plasma concentrations of homocysteine in linear fashion.

It has been hypothesized that homocysteine may 1) act as a thrombogenic agent, 2) impair the production of enthothelium-derived relaxing factor, and 3) stimulate proliferation of smooth cells, a key component in atherogenisis.

Garlic preparations are known to possess many beneficial effects in maintaining good health conditions, such as resistance against infections, lowering cholesterol levels, detoxifying harmful substances, relieving stress and enhancing the immune response. One such commercially available product is KYOLIC®, available from Wakunaga of America Co., Ltd., a subsidiary of Wakunaga Pharmaceutical Co., Ltd., and containing Aged Garlic Extract™. However, garlic products, including KYOLIC®, have never been reported to exhibit the beneficial effect on the serum homocysteine levels.

As cardiovascular disease is a prominent cause of death in industrialized countries, any factor which may affect the plasma homocysteine concentration is of great importance to public health. Although the screening of the effective materials to reduce plasma homocysteine level without any adverse effects has been continuously and actively searched, true effective materials have not been discovered yet. There have been no published reports on plant materials such as the family of Liliaceae, genus of Allium.

It is thus an object to provide an improved method and composition for oral administration to mammals (humans) which reduces the concentration of serum homocysteine.

Another object of this invention is the provision of an improved novel method of reducing the concentration of serum homocysteine in mammals by the oral administration of Allium or extracts of Allium in an acceptable pharmaceutically acceptable carrier and in a therapeutic amount.

Yet another object of this invention is to provide an improved and novel product for reducing the concentration of serum homocysteine in mammals by the oral administration of Allium or extracts of Allium in combination with vitamin $B_{12}$, vitamin $B_6$ and folic acid in an acceptable pharmaceutically acceptable carrier and in a therapeutic amount.

BRIEF DESCRIPTION OF THE INVENTION

The above and other objects of this invention are accomplished in accordance with this invention by an improved method involving oral administration to mammals (humans) of a therapeutically effective amount of a plant product derived from the genius Allium. The beneficial qualities of the Allium may preferably be enhanced by oral administration of vitamin $B_{12}$, vitamin $B_6$ and folic acid in a pharmaceutically acceptable carrier and in a therapeutic amount.

The method and product of this invention are effective for reducing, preventing or ameliorating elevated plasma homocysteine level in mammals (humans) by administering orally a therapeutically effective amount of the plant material or extracts thereof and which are generally less toxic than synthesized pharmaceuticals.

As the result of screening and testing a wide variety of Allium plants and their effective extracts, it has been discovered in accordance with this invention, that the Allium plants and their extracts have significant effect on the reduction of plasma homocysteine level when administered orally in a therapeutically effective amount.

It has also been discovered in accordance with this invention that the effect of the Allium material may be enhanced through its combination with at least one of and preferably all three of vitamin $B_{12}$, vitamin $B_6$ and folic acid.

This invention has many other advantages, and other objectives, which may be more clearly apparent from consideration of the various forms in which it may be embodied. Certain versions of such forms are described herein and form a part of the present specification. These forms will now be described in detail for the purpose of illustrating the general principles of the invention; but it is understood that such detailed description is not to be taken in a limiting sense.

DETAILED DESCRIPTION OF THE INVENTION

In accordance with the present invention, Allium plants of the family of Liliaceae, genus of Allium, such as *Allium sativum L.* (garlic), *Allium cepa* (onion), *Allium chinense* and *Allium ampeloprasum* (great headed garlic/elephant garlic) and other similar plants are used. The most suitable plant for this invention and a preferred plant is *Allium sativun L.* (garlic). The portion of the bulb of the plant is preferably used, as will be described. These materials may be dried or used as the material for the extraction, as will be described. In addition, the materials derived from the cell culture of the identified plants may also be utilized in accordance with this invention. Regardless of the Allium plant used, it is preferred that the plant be organically grown to minimize the possible presence of contaminants.

In accordance with this invention, one may use powdered garlic, or the other Allium plant materials described, which is formed by cutting, freeze-drying or air drying at a temperature not exceeding 65° and then powdered.

The various Allium plant materials mentioned may also be used in the form of extracts which typically are solvent or aqueous extracted. In a preferred form of this invention, the extract of the Allium plants is the extract from the described plants using water or alcohol or mixtures thereof in the extraction process. The extract may be prepared at room temperature for a period of time ranging from a few days to a few years. The Allium plants used in the extraction may be skinned and/or crushed with or without a moderate temperature for efficient extraction. If necessary, the Allium plants may be crushed and homogenized to produce the plant juice after heating in warm water. Oxidized iron may be added to the juice to eliminate both water soluble protein portions and fructan, with further processing.

It is preferred in accordance with this invention that the Allium plant and preferably garlic, be extracted from aqueous alcohol at room temperature for between three months and two years. The alcohol used in the extraction is usually anhydrous or hydrous alcohol, using an alkyl or alkenyl alcohol of between 1 and 4 carbon chain length. Of these alcohols, hydrous ethyl alcohol is preferred for reasons of product safety. The thus prepared extract may be used as is, concentrated into a concentrate, or in powdered form after concentration under vacuum or liophilization.

The dosage level of the material of this invention may vary according to age, body weight and body condition of the human recipient. A recommended dose is the oral administration of 100 mg to 10 g per day for adults as a powdered preparation of the Allium plants or extracts thereof, the latter being the principal pharmaceutically active component. Dosage levels based on body weight may also be calculated from the relative amounts used in the animal tests to be described.

Animal studies demonstrated the efficacy of the product and method of this invention. Growing male rats of Sprague-Dawley strain (120–180 grams) purchased from a commercial source were used throughout the study. The animals were fed an amino acid defined diet containing succinylsulfathiozole (10 g/kg diet), but no folic acid, or the same diet supplemented with 4% by weight of garlic in the form of Aged Garlic Extract™, available from Wakunaga of America Co., Ltd., (garlic extract extracted for more than one year) or diet/vitamin $B_6$ (8 mg/kg diet) or vitamin $B_{12}$ (50 μg/kg diet) or folic acid (5 mg/kg diet), or the extract and the vitamins and the folic acid in the amounts specified. The animals were fed ad labium and had access to water at all times. The feeding lasted for four weeks.

At the conclusion of the feeding, the rats were fasted overnight and blood drawn from the inferior vena cava under anesthetic conditions using ether. Blood samples were kept on ice and centrifuged at 200 xg for five minutes at 4° C. within one hour of collection. Plasma were collected and stored at −80° C. until analysis. This preparation was followed strictly for the purpose of preventing an increase or plasma homocysteine released by erythrocytes. Plasma concentration of total homocysteine was determined by the HPLC-fluorescence method of Vester and Rasmussen.

The data are as follows:

| Treatment | Plasma Homocysteine Level (μmoles/l) |
| --- | --- |
| 1. Control | 42.4 |
| 2. Garlic Extract (4% in diet) | 10.0 |
| 3. Vitamin $B_6$ (8 mg/kg diet) | 32.2 |
| 4. Vitamin $B_{12}$ (50 μg/kg diet) | 28.9 |
| 5. Folic acid (5 mg/kg diet) | 15.4 |
| 6. 2 + 3 + 4 + 5 | 4.3 |

These data indicate that the garlic extract (Allium plant extract) alone brought about a greater reduction in plasma homocysteine concentration in the test animals than did any one of either of the two vitamins or folic acid alone. The result for the garlic extract and each of the vitamins and folic acid is striking and represents almost a 90% reduction of plasma homocysteine concentration as compared to the control. These data also indicate that elevated levels of plasma homocysteine may be markedly reduced by an Allium plant material or extract used alone or in combination with the vitamins discussed and folic acid.

In accordance with this invention, it is intended that the Allium product described be administered orally to a human and preferably on a daily basis, in one or more capsules, gel capsules, or tablets, or in liquid form or in any other pharmaceutically acceptable form. The material(s) may be admixed with any one of a series of known pharmaceutically accepted carriers. Regardless of the form of oral administration, the following represents the preferred daily dosage and the range of recommended dosage, bearing in mind that body weight is a factor in the dosage.

| Material | Preferred Amount | Range |
|---|---|---|
| Aged Garlic Extract ™ powder: | 700 mg | 100 mg to 10,000 mg |
| Vitamin $B_{12}$: | 200 µg | 20 µg to 5,000 µg |
| Vitamin $B_6$: | 10 mg | 1 mg to 100 mg |
| Folic Acid: | 400 µg | 20 µg to 10,000 µg |

As noted, taken orally and in the range above described, the combination of the Allium plant material such as garlic, in the forms described, and the vitamins and folic acid, has been demonstrated to reduce substantially the plasma level of homocysteine and thus prevent or treat or ameliorate cardiovascular diseases such as myocardial infarction, stroke and multiple arteriosclerosis. It is also apparent that one may use the Allium plant material such as garlic, in the forms described, without the vitamins and folic acid or the Allium plant material and one or some of the vitamins and folic acid. Due to the marked effect that the Allium plant products, especially garlic, has demonstrated, other dietary supplements may be added to the active material, if desired. It is also the case that more than one plant material from the genus Allium or extracts of the same may be used, although it is preferred to use *Allium sativum L.* (garlic) or extracts of the same.

It is also the case that various other pharmaceutically accepted materials may be added, e.g., excipients etc., as is known in the art.

It should be understood that this invention is not limited to the detailed descriptions set forth herein which describe in detail preferred forms of the present invention. Modifications thereof will be apparent to those skilled in the art, based on the above detailed disclosure, but such modifications based on this disclosure may not be deemed to depart from the spirit and scope of the present invention as set forth in the appended claims.

What is claimed is:

1. The method of reducing the plasma homocysteine level in mammals to a value of below about 15.4 µmoles per liter comprising orally administering a therapeutically effective amount of a composition containing as the active ingredient at least one Allium plant or an extract of at least one Allium plant in admixture with a pharmaceutically accepted carrier.

2. The method as set forth in claim 1 wherein said composition further includes a therapeutically effective amount of at least one of vitamin $B_{12}$, vitamin $B_6$ and folic acid.

3. The method as set forth in claim 1 wherein said composition further includes a therapeutically effective amount of each of vitamin $B_{12}$, vitamin $B_6$ and folic acid.

4. The method as set forth in claim 1 wherein said Allium plant or extract of at least one Allium plant is selected from the group consisting of *Allium sativum L.* (garlic), *Allium cepa* (onion), *Allium chinense* and *Allium amnpeloprasum* (great headed garlic/elephant garlic).

5. The method as set forth in claim 1 wherein said composition includes between 100 mg and 10,000 mg of said Allium plant or extract and is administered orally on a daily basis.

6. The method as set forth in claim 5 wherein said composition further includes each of vitamin in $B_{12}$, vitamin $B_6$ and folic acid, said vitamin $B_{12}$ being present in an amount of between 20 µg and 5,000 µg, vitamin $B_6$ being present in an amount of between 1 mg and 100 mg and folic acid being present in amount of between 20 µg and 10,000 µg, said amounts being based on administration on a daily basis.

7. The method as set forth in claim 1 wherein said composition includes at least 700 mg of said Allium plant or extract and is administered orally on a daily basis.

8. The method as set forth in claim 7 wherein said composition further includes each of vitamin $B_{12}$, vitamin $B_6$, and folic acid, said vitamin $B_{12}$ being present in an amount of 200 µg, vitamin $B_6$ being present in an amount of 10 mg and folic acid being present in amount of 400 µg, said amounts being based on administration on a daily basis.

9. The method as set forth in claim 1 wherein said Allium plant or Allium extract is *Allium sativum L.* (garlic).

* * * * *